(12) United States Patent
Gramnäs

(10) Patent No.: US 7,052,519 B1
(45) Date of Patent: May 30, 2006

(54) PROSTHETIC LEG AND FOOT APPARATUS

(75) Inventor: Finn Gramnäs, Kinna (SE)

(73) Assignee: Gramtec Innovation AB (SE)

( * ) Notice: Subject to any disclaimer, the term of this patent is extended or adjusted under 35 U.S.C. 154(b) by 270 days.

(21) Appl. No.: 10/018,046

(22) PCT Filed: Jun. 9, 2000

(86) PCT No.: PCT/SE00/01208

§ 371 (c)(1),
(2), (4) Date: May 7, 2002

(87) PCT Pub. No.: WO00/76429

PCT Pub. Date: Dec. 21, 2000

(30) Foreign Application Priority Data

Jun. 10, 1999  (SE) .................................. 9902193

(51) Int. Cl.
*A61F 2/66* (2006.01)
(52) U.S. Cl. .......................................... 623/52; 623/53
(58) Field of Classification Search .................. 623/52, 623/47–51, 39–46; 627/53–56
See application file for complete search history.

(56) References Cited

U.S. PATENT DOCUMENTS

| 2,470,480 | A | * | 5/1949 | Fogg | ............................ | 623/26 |
| 2,749,557 | A |   | 6/1956 | Riddle |   |   |
| 3,754,286 | A |   | 8/1973 | Ryan |   |   |
| 3,851,337 | A |   | 12/1974 | Prahl |   |   |
| 4,463,459 | A | * | 8/1984 | Shorter et al. | ................. | 623/47 |
| 4,499,613 | A |   | 2/1985 | Yarrow |   |   |
| 5,112,356 | A | * | 5/1992 | Harris et al. | ................... | 623/49 |
| 5,139,525 | A | * | 8/1992 | Kristinsson | ................... | 623/55 |
| 5,258,038 | A |   | 11/1993 | Robinson et al. |   |   |
| 5,376,133 | A | * | 12/1994 | Gramnas | ..................... | 623/38 |
| 5,888,239 | A | * | 3/1999 | Wellershaus et al. | ......... | 623/55 |
| 5,941,913 | A | * | 8/1999 | Woolnough et al. | .......... | 623/47 |

(Continued)

FOREIGN PATENT DOCUMENTS

DE   818828   10/1951

(Continued)

OTHER PUBLICATIONS

International Search Report mailed from the Swedish Patent Office on Sep. 14, 2000.

(Continued)

*Primary Examiner*—Alvin J. Stewart
(74) *Attorney, Agent, or Firm*—Jansson, Shupe, Munger & Antaramian, Ltd.

(57) ABSTRACT

The present invention relates to an arrangement for a leg prosthesis (10) provided with a foot (12), which is connected to the leg prosthesis via an articulated axle (11), whereby first means (13, 14, 16–18, 30–33, 38) are arranged to provide a limited rotation of the foot relative the leg prosthesis from an initial position, in which position the leg prosthesis and the foot have a fixed angle relative each other, and second means (16–26) are arranged to provide a stepless adjustment of the fixed angle between the leg prosthesis and the foot in the initial position. According to the invention the first means (13, 14, 16–18, 30–33, 38) comprise a resilient element (14), which first end thereof is connected to the foot (12) via an elongated element (13) and which second end is connected to the leg prosthesis so that the leg prosthesis can be rotated relative the foot against the effect of the spring force of the resilient element.

14 Claims, 3 Drawing Sheets

U.S. PATENT DOCUMENTS

Figure 1:
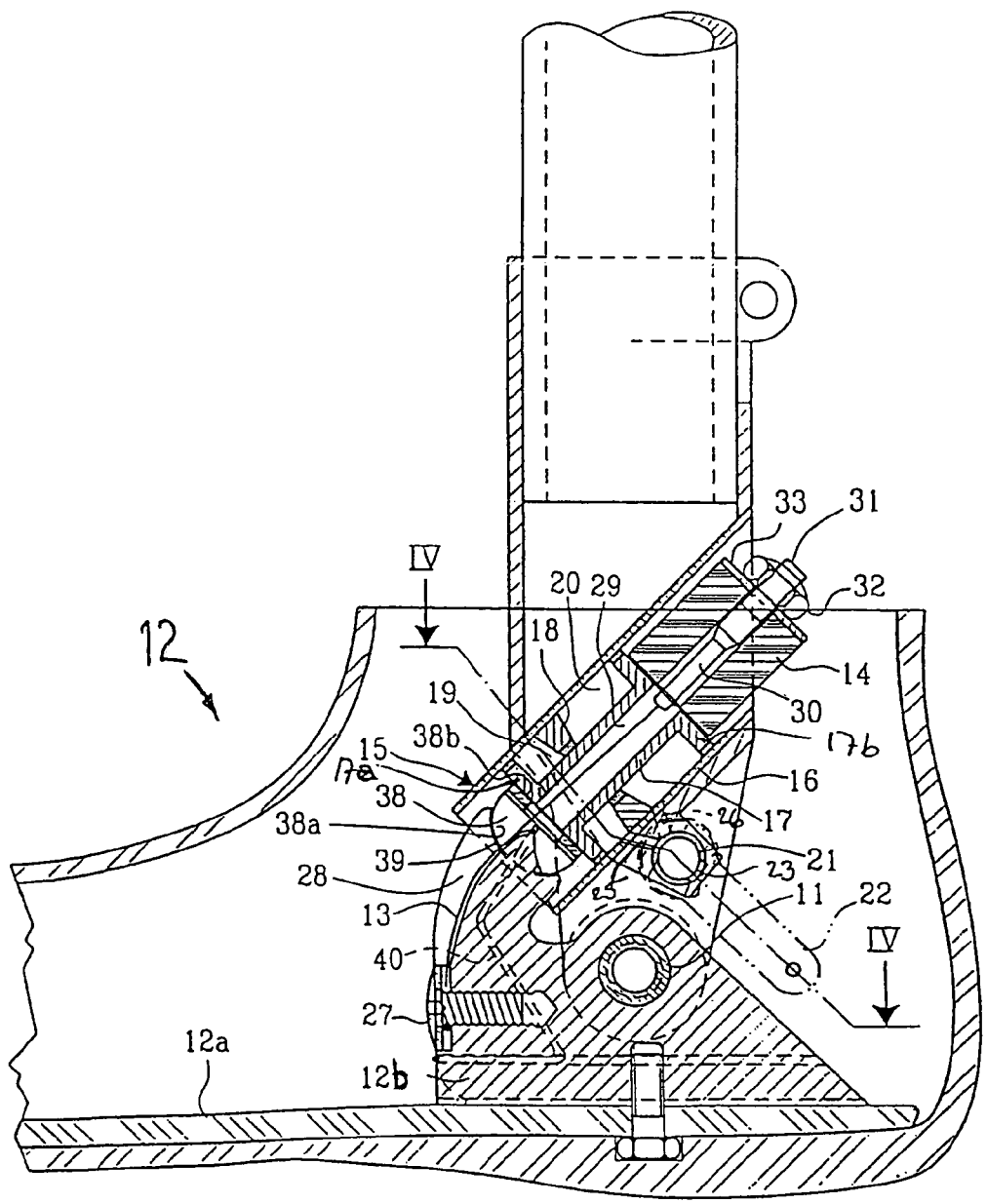

| | | | |
|---|---|---|---|
| 5,957,981 A | 9/1999 | Gramnas | |
| 6,187,052 B1 * | 2/2001 | Molino et al. | 623/52 |
| 6,436,149 B1 * | 8/2002 | Rincoe | 623/47 |
| 2002/0143407 A1 | 10/2002 | Kuiken | |

FOREIGN PATENT DOCUMENTS

| | | | |
|---|---|---|---|
| DE | 838480 | | 5/1952 |
| FR | 800547 | | 7/1936 |
| JP | 11-345 | * | 6/1999 |
| SE | 456134 | | 9/1988 |
| SE | 469780 | | 9/1993 |
| SE | 511750 | | 8/1996 |
| WO | WO 88/06431 A1 | | 9/1988 |
| WO | WO 91/15171 A1 | | 10/1991 |
| WO | WO 96/25898 A1 | | 8/1996 |

OTHER PUBLICATIONS

International Preliminary Examination Report mailed from the Swedish Patent Office on Jun. 15, 2001.

* cited by examiner

PROSTHETIC LEG AND FOOT APPARATUS

TECHNICAL FIELD

The present invention relates to a device in a leg prosthesis provided with a foot, which is connected to the leg prosthesis via an articulated axle, whereby first means are arranged to provide a limited rotation of the foot relative the leg prosthesis from an initial position, in which position the leg prosthesis and the foot have a fixed angle relative each other, and second means are arranged to provide a step-less adjustment of the fixed angle between the leg prosthesis and the foot in the initial position.

BACKGROUND OF THE INVENTION

It is well known among prosthesis wearers that downhill walking is problematic. If the prosthesis wearer does not have the possibility of adjusting the angle of the foot, the walk downhill gets such that only the heel has contact with the ground. Above a certain degree of foot angle it is difficult to bear up the body weight so that the knee does not collapse because of the lack of essential groups of muscles. Therefore, prosthesis wearers often choose to walk sidewards when walking downhills.

Further, prosthesis wearers utilizing a foot prosthesis which is not vertically adjustable have problems changing to another shoe with a different heel height, and have difficulty walking without shoes. Individual, vertical adjustment of the foot is desirable because such adjustability can reduce problems with pain in the user's back and can minimize wear on the user's hips.

Through for instance U.S. Pat. No. 2,749,557 is known an adjustable foot, however it is only adjustable to three different angular positions.

Furthermore, SE-B-456 134 shows a prosthesis foot where the angular positions of the foot are adjusted with a screw existing in the heel of the foot. The prosthesis wearer must turn the screw a number of turns to change the angle position, which requires a certain work effort. The principle of changing the angle shown in this document has the great disadvantage that the length of the leg changes, which results in that the prosthesis wearer can have one leg shorter or longer than the other in certain situations.

Further, SE-B-469 780 shows an additional example of a prosthesis foot where the angle position of the foot can be adjusted, in this case using a ball screw and ball nut.

Furthermore, WO 96/25898 shows a device of the kind mentioned in the preamble.

The invention relates to a device of the kind mentioned in the preamble, which can easily be adjusted to the weight and walk pattern of the prosthesis wearer and which is reliable and simple and cheap to manufacture.

SUMMARY OF THE INVENTION

This aim is achieved by means of a device in a leg prosthesis provided with a foot, which is connected to the leg prosthesis via an articulated axle, whereby first means are arranged to allow a limited rotation of the foot relative the leg prosthesis from an initial position, in which position the leg prosthesis and the foot have a fixed angle relative each other, and second means are arranged to provide a step-less adjustment of the fixed angle between the leg prosthesis and the foot in the initial position, characterized in that the first means comprise a resilient element, which first end thereof is connected to the foot via a elongated element and which second end is connected to the leg prosthesis so that the leg prosthesis can be rotated relative the foot against the effect of the spring force of the resilient element.

In a preferred embodiment the second means comprise a displacable element, which is displacably arranged relative the leg prosthesis, and means to hold the displacably arranged element in a desired displacement position, whereby the displacable element, set in its initial position, in one end bears on a portion of the foot and in its other end on the resilient element. The displacable means is formed by a piston with outwardly directed ring flanges, which piston is displacably arranged in a cylinder attached to the leg prosthesis, and the means for holding the piston in a desired displacement position relative the cylinder is formed by a ring wall projecting inwards from the cylinder, which wall divides the space between the ring flanges of the piston in two chambers, and a two-way valve, which in opened position provides flow of the medium existing in the chambers between these and in closed position prevents such flow. The elongated element extends through a central axial channel in the piston and through a central axial passage in the resilient element and is connected, via a washer of rigid material, to that end of the resilient element, which is opposite the end which bears on the piston. The elongated element constitutes of flexible material and can be made of a cord or wire or of a belt of a material with little extensibility.

LIST OF DRAWINGS

Figure 2:
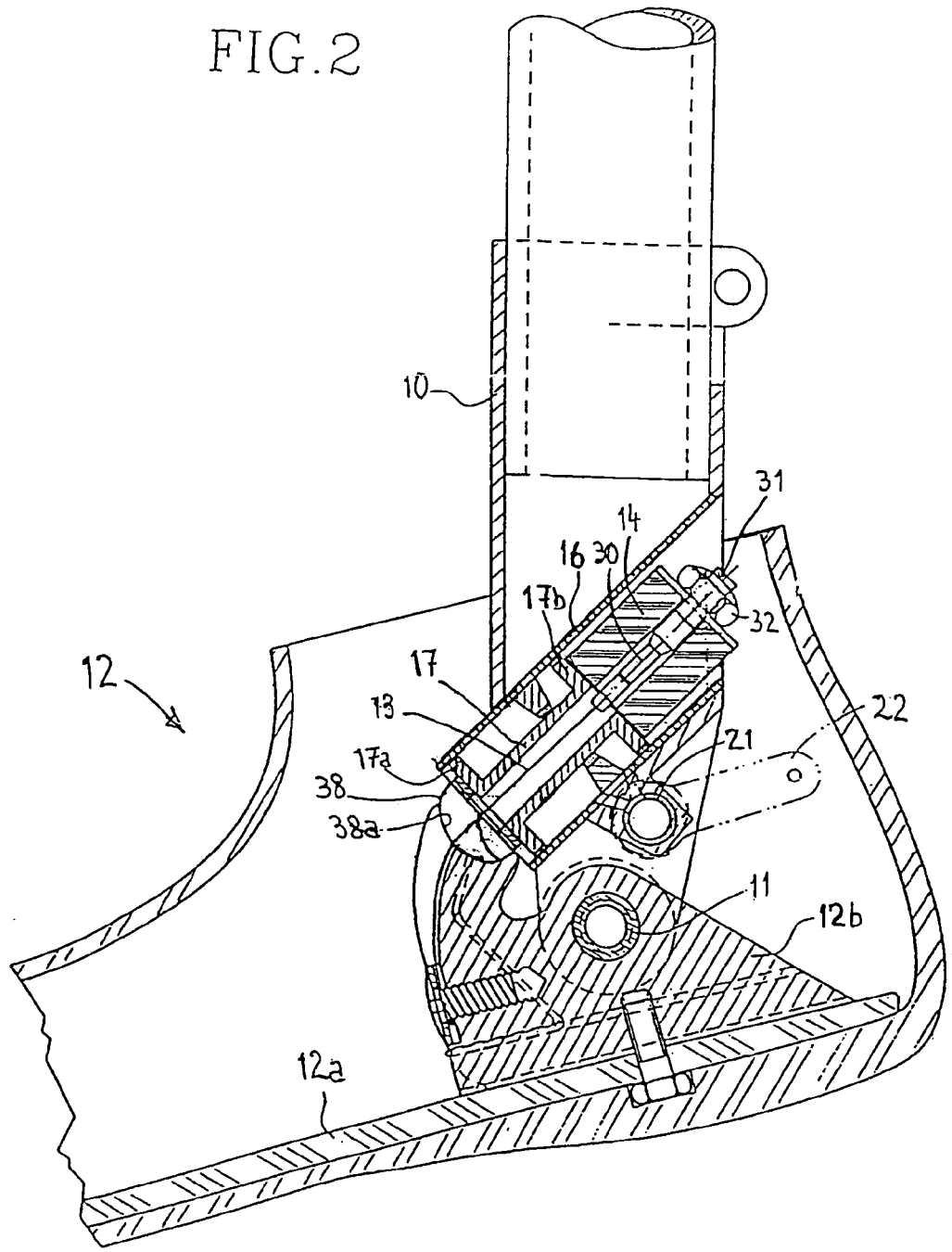
Figure 4:
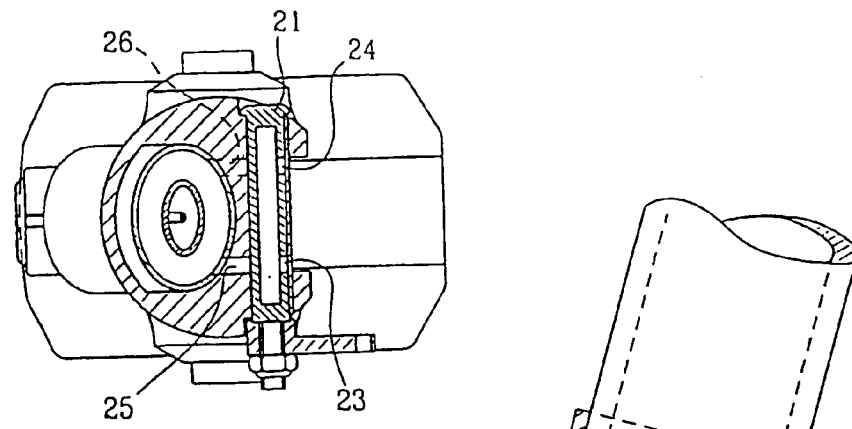
Figure 3:
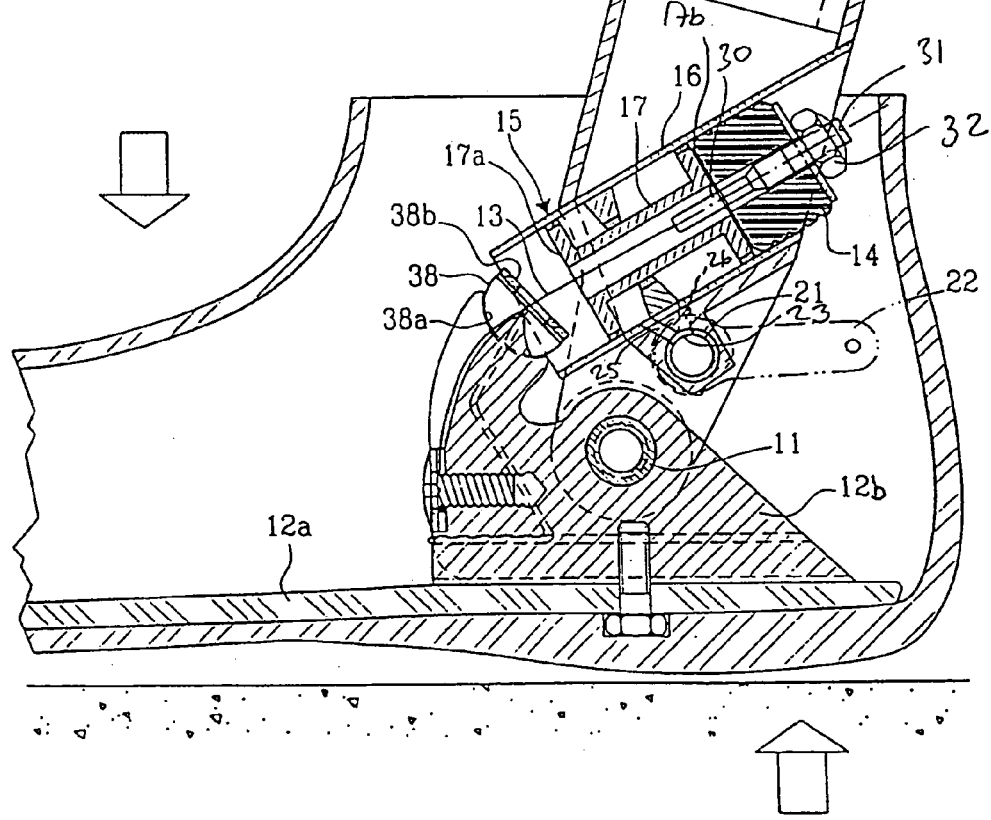

In the following the invention will be described with reference to enclosed figures, in which;

FIG. 1 shows a longitudinal cross section through a foot and leg prosthesis according to an embodiment of the invention in an unloaded position, FIG. 2 shows a section corresponding to FIG. 1, but in another initial position for the angle between foot and leg prosthesis, FIG. 3 shows the foot and leg prosthesis according to FIG. 1 just after the foot prosthesis has been set down, and FIG. 4 is a section along line IV—IV in FIG. 1.

DESCRIPTION OF EMBODIMENTS

The Figures show a leg prosthesis 10 in the form of cylindrical tube frame, which via an articulated axle 11, forming an ankle joint, is connected to a portion 12b of a foot 12. The foot 12 can be provided with a foot blade 12a, which can be provided with foot cosmetics. The elongate element 13, in the form of a cord, wire, belt or the like, is eccentrically attached to the portion 12b of the foot relative its articulated axle 11. The elongate element 13 runs through a central channel 29 running through a piston 17 and is attached to a nipple 30 with its second end, which nipple 30 extends through a central passage in resilient element 14. A screw 31 is threaded into the nipple 30 and a nut 32 is screwed on the outside of the screw. Preferably, a washer 33 of metal or other rigid material is provided between the nut 32 and the resilient element 14. Suitably, the elongate element 13 has such a length that the resilient element 14 is restrained between one end 17b of the piston 17 and the washer 33 in a somewhat compressed state. FIG. 1 shows the leg 10 and the foot 12 in the initial position, in which the angle between these parts is about 90°. In the initial position the end 17a of the piston 17 bears onto a half spherical body 38, which rests in a cup-shaped recess in the foot portion 12b.

The piston 17 and the resilient element 14 extend inside a cylinder 16, which diagonally extends through the lower part of the leg prosthesis above the articulated axle 11. The ends 17a, 17b of the piston 17 are formed by outwardly directed ring flanges, which edges sealingly bear against the wall of the cylinder 16. The cylinder 16 has an inwardly directed ring wall 18, which is arranged between the ring flanges of the piston 17 and which sealingly bears against the tube wall of the piston 17. The ring wall 18 of the cylinder and the respective ring flanges 17a, 17b of the piston delimit two ring chambers 19, 20, which are filled with hydraulic medium. These ring chambers can communicate with each other by means of an overflow valve 21. The overflow valve 21 is adjustable between opened and closed position by means of an adjustable lever 22 on the outside of the leg prosthesis.

In the shown embodiment, the overflow valve 21 is formed by a rotatable cylindric valve body with two openings 23 and 24, which in the opened position of the valve (FIG. 1) are facing and communicating via holes 25 and 26 in the wall of the cylinder with one chamber 19 and 20 respectively each. Thus, the chambers communicate with each other in this position and overflow of hydraulic medium can exist between the chambers. In another position, which is shown in FIGS. 2, 3 and 4, the valve 21 is closed whereby the openings 23 and 24 are facing away from the holes 25 and 26.

One end of the elongate element 13 is attached to the front portion of the foot portion 12b by means of an attachment screw 27 and runs through a curved slot 28 in said portion, which works as direction changer. The elongate element 13 further runs through the half spherical body 38, which has a curved surface 38a, which cooperates with and can rotate in a cup-shaped support surface 39 at the foot portion 12b, and a plane surface 38b, which cooperates with the end 17a of the piston 17. The body 38 is kept in place in the foot portion 12b by means of a spring 40. In the initial position according to FIG. 1, the end surface 17a of the piston 17 is pressed into contact with the plane surface 38b of the body 38 because of the preload applied to the resilient element 14 by the piston 17 and the washer 33 and nut 32. The foot is also substantially unloaded in the heel portion. In the position shown in FIG. 1, the piston 17 is displacable relative the cylinder 16. After the lever 22 has been brought up to the closed position of the valve 21, the piston 17 can no longer be displaced relative the cylinder 16 and the leg prosthesis provided with a foot is in its usage position.

When setting down a foot during walking, the heel is first set down and thereafter the weight is successively brought over to that foot, which was just set down. In the position shown in FIG. 3 the foot has just been set down and the transfer of weight has just begun. During the transfer of weight to the set down leg, the upward force on the heel will generate a moment, such as is indicated with arrows in FIG. 3, that by effect of the spring force in the resilient element 14 will rotate the foot downwards until the foot blade 12a comes into contact with the ground. In this case, the resilient element 14 works as a shock absorber that absorbs the force that arises when the heel is set down. The maximum angle that the leg prosthesis can form against the foot in the set down position in FIG. 3, is limited by the maximum possible compression of the resilient element 14. The angle that the leg prosthesis should be able to form against the foot in the set down position of FIG. 3 to provide a comfortable walk, is dependent of the length of the steps of the prosthesis wearer. The shock absorbing effect of the resilient element depends on the weight and walk pattern of the prosthesis wearer. The resilient element 14 working as shock absorber can be individually adjusted by preload that is achieved by means of varying the tightening of the nut 32 and by choosing maximum length of compression of the element. As the resilient element is easy to remove and put back, it can easily be changed to another element, which is more suitable for the body weight and walk pattern of the prosthesis wearer. Resilient elements that are worn out can easily be changed to new ones.

An unloaded foot will automatically be displaced to the initial position because of the fact that the resilient element 14 always aims to come into its expanded position.

If it is desired to change the initial position, i.e., change the angle between the leg prosthesis 10 and the foot 12, (e.g., when changing to shoes with high heels), the overflow valve 21 is opened by means of the lever 22, whereby an overflow of hydraulic medium can exist between the chambers 19 and 20. This enables the piston 17 to be continuously displaced relative to the cylinder 16 and the resilient element 14, which permits the leg prosthesis 10 to be rotated relative the foot 12 within the limits of possible displacement of the ring wall 18 of the cylinder 16 in the chambers 19, 20.

At the same time as the displacement of the piston 16 relative to the cylinder 17, the cylinder 16 will be rotated around the articulated axle 11, which is followed by a rotation of the body 38, the piston 17 and the resilient element 14. The position of the elongate element 13 in the channel 29 will also change, as is shown in the FIG. 2. The diameter of the channel 29 is sufficient to permit the relative change in position of the elongate element 13. When a desired angle between the leg prosthesis 10 and the foot 12 has been reached, the valve 21 is closed.

In practice, adjustment to a new initial position is made through that the shoe with high heel is put on the foot, whereby the valve is opened. The leg prosthesis is then placed in a vertical position and the valve is closed.

In the embodiments shown in the Figures, the resilient element 14 constitutes an elastic body 14 of e.g., rubber or other elastic polymeric material. Within the scope of the invention it is of course possible to use other types of resilient bodies, e.g., helical or cup springs. The elongate element 13 is formed of a material which does not stretch when subjected to the loads which normally exist during usage of leg prostheses and can be made of steel, plastic or textile material.

Naturally, modifications of the invention are possible within the scope of the invention. For example, the valve 21 could be manoeuvrable by an electric motor, e.g., a step motor, and the leg prosthesis could include a battery and a switch, which could be placed so that it would be easy to reach for the prosthesis wearer. Furthermore, the piston 17 could be replaced by a rigid sleeve, which runs in a cylinder provided with a slit, which cylinder is provided with a device for clamping the cylinder against the sleeve. Nor is it necessary that the elongate element 13 is resilient; elongate element 13 can instead be replaced with a rod or the like which is articulated to the body 38 and the nipple 30. Therefore, the invention should only be limited to the contents of the appending claims.

The invention claimed is:

1. A leg prosthesis having a foot pivotally connected to the leg prosthesis at a pivoting joint, said foot and leg prosthesis being relatively pivotally adjustable to facilitate walking on downwardly-angled surfaces comprising:
   means for step-less adjusting of the foot relative to the leg prosthesis such that, in an adjusted position, the foot is at a fixed angle relative to the leg prosthesis, the means for step-less adjusting comprising:
      a positioner slidably positionable with respect to the leg prosthesis, said positioner acting against the foot and leg prosthesis to provide the relative pivoting adjustment; and means for slideably positioning the positioner to a fixed position with respect to the leg prosthesis; and means for limiting pivoting movement of the foot relative to the leg prosthesis in the adjusted position during walking, the means for limiting pivoting movement comprising:

a resilient element having a first end connected to the foot by an elongate element; and the positioner slidably positions the resilient element to a fixed position with respect to the leg prosthesis such that resilient element spring force resists relative pivoting movement of the foot and leg prosthesis.

2. The prosthesis of claim 1 wherein:

the positioner comprises a piston with outwardly directed ring flanges, said piston being displacably arranged in a cylinder attached to the leg prosthesis; and the positioning means comprises a ring wall projecting inwardly from the cylinder, said wall dividing the space between the ring flanges of the piston into two chambers, and a two-way valve, which in an opened position provides flow of a medium existing in the chambers between said chambers and in a closed position prevents such flow.

3. The prosthesis of claim 2 wherein the elongate element extends through a central axial channel in the piston and through a central axial passage in the resilient element and is connected, via a washer of rigid material, to that end of the resilient element, which is opposite the end which bears on the piston.

4. The prosthesis according to any of the preceding claims wherein the elongate element is made of a flexible material.

5. The prosthesis of claim 4 wherein the elongate element is made of a material selected from the group consisting of cord, wire, and a belt of a material with little extensibility.

6. A prosthesis comprising:

a leg element;

a foot element pivotally joined to the leg element at a pivoting joint and having front and rear ends;

a cylinder at least partially within the foot element secured in fixed-position relationship to the leg element;

a position-adjustable resilient element positionable within the cylinder to a fixed position corresponding to a selected position of the foot element relative to the leg element; and a linkage joining the resilient element to the foot element such that downward pivoting movement of the foot element front end within a walking range compresses the resilient element and the resilient element limits said downward pivoting movement.

7. The prosthesis of claim 6 further comprising a positioner positionable within the cylinder to a selected position, the resilient element bearing against the positioner to provide position adjustment thereof.

8. The prosthesis of claim 7 wherein the positioner comprises:

a piston positionable within the cylinder having a body and front and rear end walls joined thereto, the body, end walls and cylinder defining a piston space between the piston and cylinder;

a cylinder wall in sealing relationship with the piston body permitting movement of the piston with respect thereto and separating the piston space into front and rear chambers; and a hydraulic medium controllably flowable between the front and rear chambers such that flow of the medium to the front chamber slides the piston rearward in the cylinder and flow of the medium to the rear chamber slides the piston forward in the cylinder and stoppage of medium flow positions the piston in the selected position.

9. The prosthesis of claim 8 further comprising a valve controlling the medium flow between the front and rear chambers, the valve having an open position permitting medium flow and a closed position preventing medium flow thereby positioning the piston in the selected position.

10. The prosthesis of claim 9 wherein:

a resilient element front end bears against a piston rear end;

the linkage is an elongate element having a first end joined to the foot element forward of the pivoting joint and a second end joined to a resilient element rear end such that the elongate element:

transfers force to the resilient element rear end during downward movement of the foot front end thereby compressing the resilient element positioned against the piston; and transfers resilient element spring force to the foot element when the foot element is unloaded thereby returning the foot element to the selected position.

11. The prosthesis of claim 10 further comprising:

a foot support portion carrying the pivoting joint and secured within the foot element, said foot support portion having a front surface forward of the pivoting joint;

a bearing surface along the foot support portion forward of the pivoting joint structured to support the elongate element bearing thereon, said bearing surface including an elongate element attachment point on the front surface, a direction-changing portion adapted to change direction of the elongate element and direct the elongate element from the front surface toward the resilient element and a bearing portion therebetween; and the elongate element bears against the bearing surface between the attachment point and direction-changing portion.

12. The prosthesis of claim 11 wherein the elongate element is selected from the group consisting of a cord, a wire and a belt.

13. The prosthesis of claim 11 wherein:

the piston defines a piston central axial passageway extending therethrough;

the resilient element defines a central axial passageway extending therethrough aligned with the piston passageway;

the elongate element extends within the passageways; and a nipple in the resilient element passageway has a first end joined to the elongate element and a second end bearing against the resilient element rear end.

14. The prosthesis of claim 13 further comprising:

a cup-shaped support surface formed in the foot support portion proximate a cylinder front end; and a piston support having a cup-shaped end movably seated in the cup-shaped support surface and a flat end positioned against the piston front wall when the foot element is unloaded.

* * * * *